(12) United States Patent
Ferguson, III et al.

(10) Patent No.: US 11,373,742 B2
(45) Date of Patent: Jun. 28, 2022

(54) AUGMENTED REALITY PHARMACY SYSTEM AND METHOD

(71) Applicant: Change Healthcare Holdings LLC, Nashville, TN (US)

(72) Inventors: Clinton S. Ferguson, III, Arlington, TX (US); Shrikant M. Patel, Irving, TX (US); Brandi D. Sherill, Springtown, TX (US); Tara L. Long, Haslet, TX (US); Aaron D. Howard, Fort Worth, TX (US); Brad T. Crosslin, Keller, TX (US)

(73) Assignee: CHANGE HEALTHCARE HOLDINGS LLC, Nashville, TN (US)

( * ) Notice: Subject to any disclaimer, the term of this patent is extended or adjusted under 35 U.S.C. 154(b) by 267 days.

(21) Appl. No.: 16/549,872

(22) Filed: Aug. 23, 2019

(65) Prior Publication Data

US 2021/0057070 A1 Feb. 25, 2021

(51) Int. Cl.
| | |
|---|---|
| G16H 20/10 | (2018.01) |
| G06T 19/00 | (2011.01) |
| G06V 20/20 | (2022.01) |
| G06T 11/60 | (2006.01) |
| G06F 3/01 | (2006.01) |
| G02B 27/01 | (2006.01) |
| G06V 40/16 | (2022.01) |

(52) U.S. Cl.
CPC ......... *G16H 20/10* (2018.01); *G02B 27/0172* (2013.01); *G06F 3/017* (2013.01); *G06T 11/60* (2013.01); *G06T 19/006* (2013.01); *G06V 20/20* (2022.01); *G06V 40/165* (2022.01); *G02B 2027/0178* (2013.01)

(58) Field of Classification Search
None
See application file for complete search history.

(56) References Cited

U.S. PATENT DOCUMENTS

| 8,965,460 B1* | 2/2015 | Rao | H04N 1/00307 |
| | | | 455/566 |
| 10,821,054 B1* | 11/2020 | Howton | A61J 7/0481 |
| 2004/0122712 A1* | 6/2004 | Hill, Sr. | G06Q 10/10 |
| | | | 705/2 |
| 2005/0187822 A1* | 8/2005 | Lapsker | G06Q 30/0221 |
| | | | 705/14.22 |

(Continued)

*Primary Examiner* — David H Chu
(74) *Attorney, Agent, or Firm* — Myers Bigel, P.A.

(57) ABSTRACT

An augmented reality pharmacy system and method for assisting pharmacy personnel with health care-related tasks is presented. The augmented reality pharmacy system can reduce or eliminate common pharmacy fulfillment errors attributable to human error. The present disclosure improves pharmacy fulfilment error rates by providing image processing systems adapted to characterize prescription and drug related information to verify prescription fulfillment; incorporates augmented reality systems with pharmacy systems to provide enhanced fulfillment systems where real-world objects can be over-laid with virtual reality elements to provide additional pharmaceutical information to a user; and shortens the time spent by a user looking for a specific drug bottle in a maze of similar-looking drug bottles by incorporating wayfinding technology coupled with location based components.

20 Claims, 7 Drawing Sheets (56) References Cited

U.S. PATENT DOCUMENTS

| | | | |
|---|---|---|---|
| 2007/0299687 A1* | 12/2007 | Palmer | G16H 20/10 705/2 |
| 2008/0128496 A1* | 6/2008 | Bertranou | G06Q 10/08 235/383 |
| 2011/0288883 A1* | 11/2011 | Knoth | G06Q 10/087 705/3 |
| 2013/0218721 A1* | 8/2013 | Borhan | G06Q 30/02 705/26.41 |
| 2013/0293530 A1* | 11/2013 | Perez | G06F 3/012 345/418 |
| 2014/0040043 A1* | 2/2014 | Barron | G06Q 30/06 705/14.66 |
| 2015/0073907 A1* | 3/2015 | Purves | G06Q 20/32 705/14.58 |
| 2015/0379616 A1* | 12/2015 | Cleveland | G06Q 30/0633 705/26.8 |
| 2016/0162971 A1* | 6/2016 | Peterson | G06Q 30/0639 705/26.63 |
| 2016/0228771 A1* | 8/2016 | Watson | A61B 5/4023 |
| 2017/0323376 A1* | 11/2017 | Glaser | G06Q 20/203 |
| 2018/0107977 A1* | 4/2018 | McHale | G06Q 30/0609 |
| 2018/0121897 A1* | 5/2018 | Bacallao | G06Q 30/0601 |
| 2018/0275749 A1* | 9/2018 | Yoon | G02B 27/01 |
| 2019/0156402 A1* | 5/2019 | Greenberger | G06K 9/00671 |
| 2019/0371272 A1* | 12/2019 | Southworth | G06K 7/10722 |

* cited by examiner

AUGMENTED REALITY PHARMACY SYSTEM AND METHOD

BACKGROUND OF THE INVENTION

1. Field of the Invention

The present invention generally relates to an augmented reality system and more particularly to an augmented reality system for assisting pharmacy personnel with health care-related tasks.

2. Background of the Invention and Description of the Prior Art

A single pharmacy can receive hundreds of prescriptions to fill each day. Pharmacies, in particular, typically apply manual processes to manage and fulfill prescription-related tasks. Manual task completion is clearly insufficient for such tasks. Every year, thousands of prescription errors cost pharmacies thousands of dollars and delay proper patient treatment. At worst, pharmacy errors can have dire effects for patients if the wrong type of medication is provided, or if the prescription regimen is altered in any way. The wrong medication can be used to fill a prescription, the pill count can be incorrect, or the prescription information can be incorrectly stated.

A recent study, published in the American Journal of Health-System Pharmacy (AJHP), found that an increase in the number of orders verified per shift was associated with an increased rate of pharmacist errors during order verification in a tertiary-care medical center. The primary finding from this study was that the number of medication errors increased with the number of orders verified per pharmacist per shift. According to the findings, the verification of more than 400 orders per shift per pharmacist was associated with the highest risk of errors. Interestingly, the study found that errors occurred more often during the evening shift (10.57 per 100 shifts), followed by the day shift (7.33 errors per 100 shifts) and the night shift (4.55 errors per 100 shifts). Such pharmacy errors can lead to increased liability for pharmacies.

SUMMARY OF THE INVENTION

The present disclosure achieves technical advantages as an augmented reality system for assisting pharmacy personnel with health care-related tasks. The augmented reality pharmacy system can reduce or eliminate common pharmacy fulfillment errors attributable to human error. The present disclosure improves pharmacy fulfilment error rates by providing image processing systems adapted to characterize prescription and drug related information to verify prescription fulfillment; incorporates augmented reality systems with pharmacy systems to provide enhanced fulfillment systems where real-world objects can be over-laid with virtual reality elements to provide additional pharmaceutical information to a user; and shortens the time spent by a user looking for a specific drug bottle in a maze of similar-looking drug bottles by incorporating wayfinding technology coupled with location based components.

It is an object of the invention to provide a pharmaceutical services platform configured to capture data related to a received prescription from a wearable device to assist the pharmacist in fulfilling the received prescription.

It is a further object of the invention to provide the pharmacist information related to the received prescription on the wearable device to assist the pharmacist in fulfilling the received prescription and verify the accuracy of the fulfilment of the received prescription.

These and other objects are provided by the following embodiments.

In one embodiment, an augmented reality pharmacy system, can include: a wearable device including a transparent display, a speaker, a video camera, a microphone, and an input element, the wearable device configured so that a user can see an object through the transparent display and information related to a pharmacy task on the transparent display; and a server including computer-executable instructions configured to provide: a task management module, configured to receive a prescription fulfillment request, assign the prescription fulfillment request to the user for fulfillment, and verify the prescription fulfillment, a biometric module configured to identify the user or a patient using data captured by the wearable device, a drug identification module, configured to identify, via the server, a drug identified in the prescription fulfillment request and retrieve drug-related information from a standardized drug database related to the identified drug, a content generation module, configured to send and receive images, audio, and text related to the prescription fulfillment request to and from the wearable device, an image learning module, configured to analyze a video camera image to determine a pill count, and a way-finding module, configured to determine and display a route from the user's position to the identified drug's shelf location, on the transparent display.

In another embodiment, an augmented reality pharmacy fill station system, includes: a wearable device configured to provide information related to a pharmacy task to a user; and a server including computer-executable instructions that when executed cause the server to: receive, via the server, a fulfilment request having prescription information identifying a drug, drug dosing, drug pill count, and a patient, receive, via the wearable device over an encrypted network, an image of a drug label having drug-identifying information, verify, via the server, whether the drug-identifying information on the drug label matches the drug identified in the fulfillment request, receive, via a database, standardized drug information related to the identified drug, including a drug identifier, an image of a drug barcode, and one or more pill form images, display, via the wearable device, at least a portion of the standardized drug information, generate, via the server, an alert on the wearable device indicating whether the drug-identifying information on the drug label matches the drug identified in the fulfillment request, receive, via the wearable device, an image of a plurality of fulfilment pills, analyze, via the server, the fulfilment pill image to determine a pill count and verify that at least one of the fulfillment pills match at least one of the pill form images, and generate, via the server, an alert on the wearable device indicating whether the pill count matches the fulfillment request drug pill count.

DETAILED DESCRIPTION OF THE INVENTION

The preferred version of the disclosure presented in the following written description and the various features and advantageous details thereof, are explained more fully with reference to the non-limiting examples included in the accompanying drawings and as detailed in the description, which follows. Descriptions of well-known components have been omitted so to not unnecessarily obscure the principle features described herein. The examples used in the following description are intended to facilitate an understanding of the ways in which the disclosure can be implemented and practiced. Accordingly, these examples should not be construed as limiting the scope of the claims.

Figure 1A:
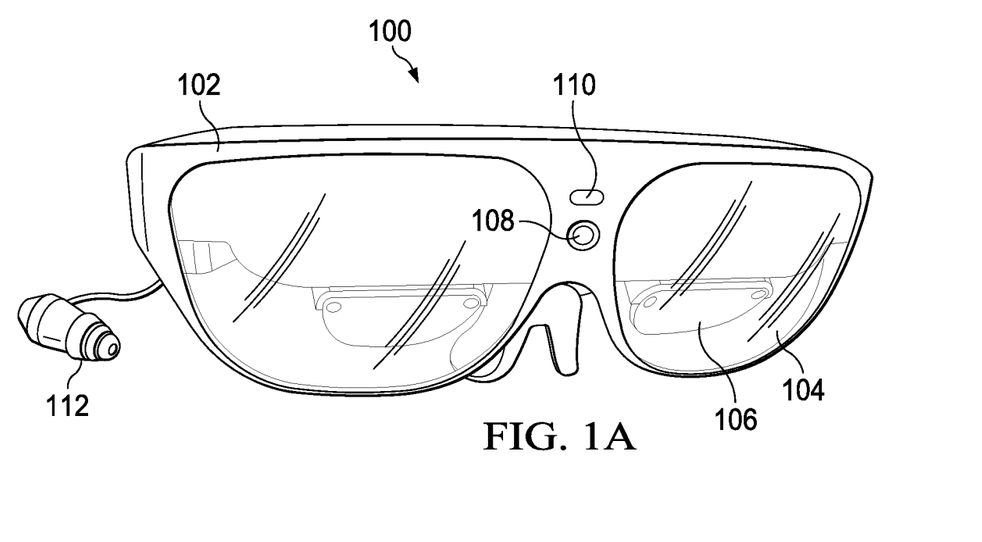
FIG. 1A illustrates a front perspective view of a wearable device, in accordance with one exemplary embodiment of the present disclosure.

FIG. 1A illustrates a front perspective view of a wearable device, generally designated as 100, in accordance with one exemplary embodiment of the present disclosure. The wearable device 100 can include a frame 102, a lens 104, a transparent display 106, a video camera 108, a microphone 110, and an earpiece 112.

The wearable device 100 can be in eyeglass form, handheld form, or other suitable form. The handheld form of the wearable device 100 can also include a mechanism, such as a frame, handle, or other attachment means to couple the device to the user. The wearable device 100 can include a rechargeable battery. The wearable device 100 can communicate via wired or wireless communication mechanism, including over Ethernet, Wi-Fi, Bluetooth, Cellular, NFC, RFID, or other suitable technology. The wearable device 100 can also include a gyroscope, accelerometer, or other suitable movement identification device. The lens 104 can be un-tinted, or tinted to provide better visibility for the transparent display 106. Alternatively, the lens 104 can be excluded, in lieu of the transparent display 106. The video camera 108 can capture still images, as well as video. The video camera 108 can include a Charge-Coupled Device (CCD), such as a CMOS or other suitable device. The wearable device 100 can have one or more video cameras 108 disposed around or inside of the wearable device 100.

Figure 1B:
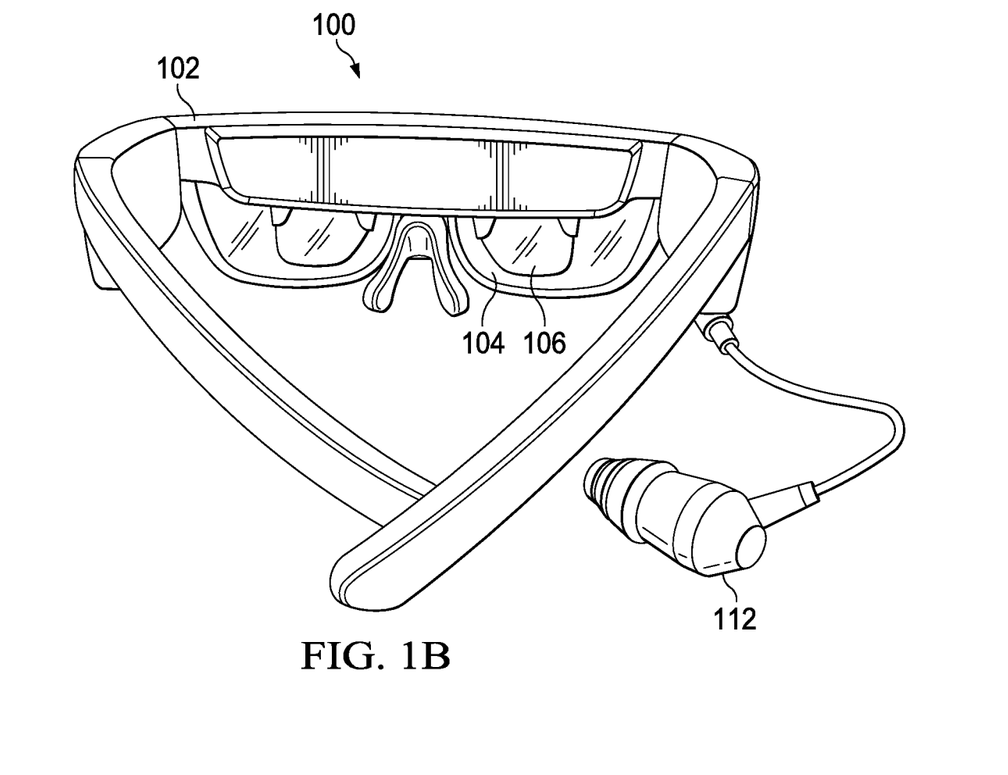
FIG. 1B illustrates a back perspective view of the wearable device, in accordance with one exemplary embodiment of the present disclosure.

FIG. 1B illustrates a back perspective view of the wearable device 100, in accordance with one exemplary embodiment of the present disclosure. The transparent display 106 can be smaller than the lens 104, or larger than the lens 104. The frame 102 can house a battery, networking components, or other suitable components. The earpiece 112 can include a speaker and a microphone. The earpiece 112 can be coupled to the frame via wired or wireless connection. The frame 102 can also include a camera to capture an image of the user, including retinal scan images, facial images, or other suitable images of the user.

Figure 1C:
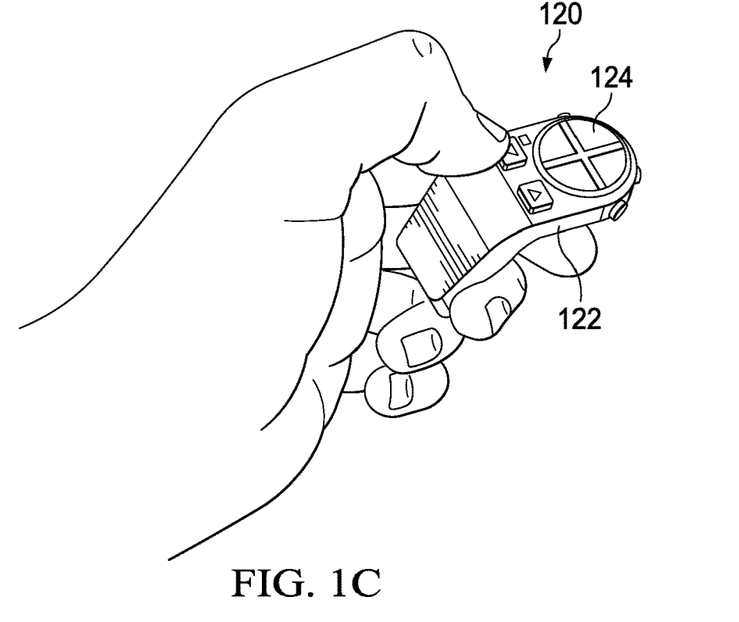
FIG. 1C illustrates a perspective view of an input element, in accordance with one exemplary embodiment of the present disclosure.

FIG. 1C illustrates a perspective view of an input element, generally designated 120, in accordance with one exemplary embodiment of the present disclosure. The input element 120 can include a handle 122 and one or more buttons 124. The input element can allow a user to navigate menu elements displayed on the transparent display 106. For example, one of the buttons 124 may allow the navigation through one or more menus displayed on the transparent display 106. Another button 124 may allow for the selection of a menu item displayed on the transparent display 106. The functionality of the buttons may vary based on the duration that a button is held, as in a tap or long-press.

Figure 2:
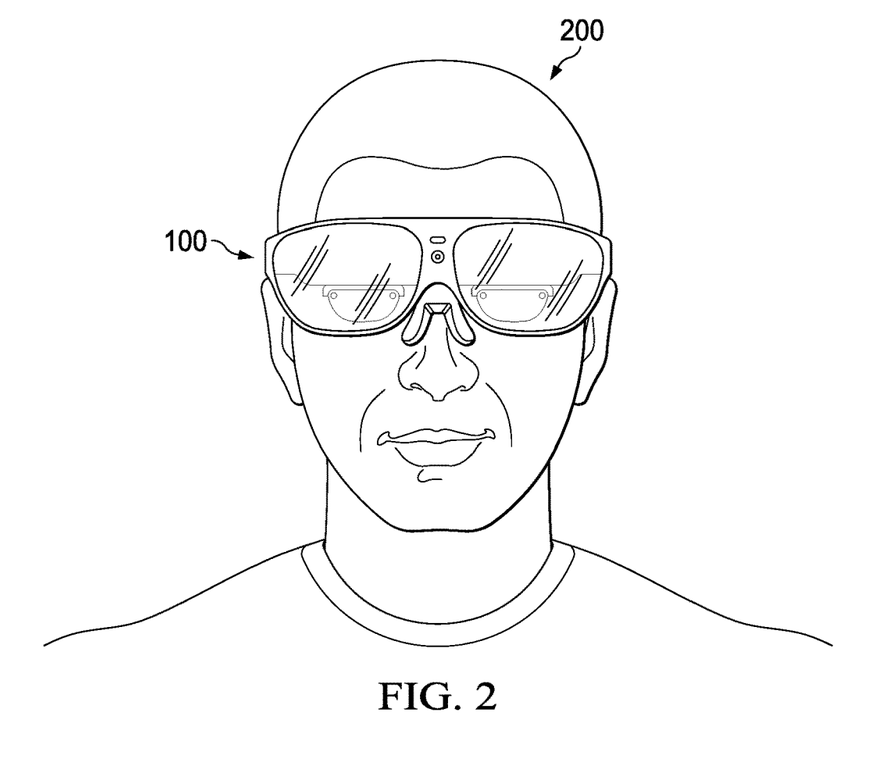
FIG. 2 illustrates a perspective view of a user wearing the wearable device, in accordance with one exemplary embodiment of the present disclosure.

FIG. 2 illustrates a perspective view 200 of a user wearing the wearable device 100, in accordance with one exemplary embodiment of the present disclosure. The wearable device 100 can be worn on a person like glasses or can be hand-held, like a magnifying glass. Alternatively, the wearable device can be coupled to a smart watch, such that a transparent window is operably coupled to the smart watch, among other suitable form factors.

Figure 3:
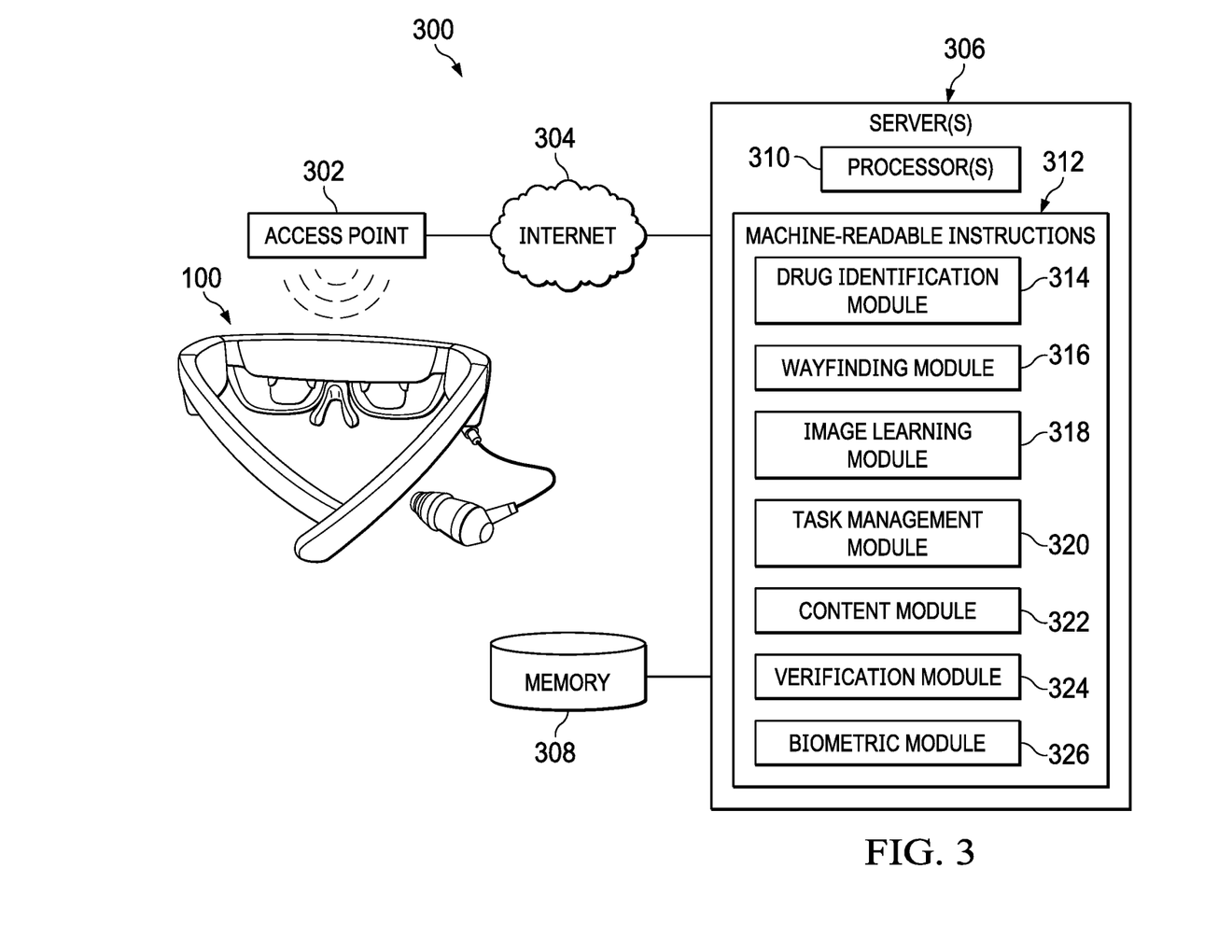
FIG. 3 illustrates a system network diagram depicting functional components of an augmented reality pharmacy system, in accordance with one exemplary embodiment of the present disclosure.

FIG. 3 illustrates a system network diagram depicting several functional components of an augmented reality pharmacy system 300, in accordance with one exemplary embodiment of the present disclosure. The augmented reality pharmacy system 300 can include the wearable device 100, an access point 302, a server 306, and a memory 308.

The access point 302 can be a wireless router, a wired switch, or other suitable networking device that can facilitate communication through the internet 304, between the wearable device 100 and the server 306. The communication can be encrypted, unencrypted, over a VPN tunnel, or other suitable communication means. The internet 100 can be a WAN, LAN, PAN, or other suitable network. The network communication between the wearable device 100 and the sever 306 can be encrypted using PGP, Blowfish, AES 3DES, HTTPS, or other suitable encryption. The access point 302 can be configured to communicate with the wearable device using Wi-Fi, Bluetooth, Ethernet, or other suitable communication protocol. Additionally, third part databases can be operably connected to the server 306 via the Internet 304.

The server 306 can be implemented in hardware, software, or a suitable combination of hardware and software therefor, and may comprise one or more software systems operating on one or more servers, having one or more processors 310, with access to memory 308. Server(s) can include electronic storage, one or more processors, and/or other components. Server(s) can include communication lines, or ports to enable the exchange of information with a network and/or other computing platforms. Server(s) can also include a plurality of hardware, software, and/or firmware components operating together to provide the functionality attributed herein to server(s). For example, server (s) can be implemented by a cloud of computing platforms operating together as server(s). Additionally, the server 306 can include memory 308.

Memory 308 can comprise electronic storage that can include non-transitory storage media that electronically stores information. The electronic storage media of electronic storage may include one or both of system storage that is provided integrally (i.e., substantially non-removable) with server(s) and/or removable storage that is removably connectable to server(s) via, for example, a port (e.g., a USB port, a firewire port, etc.) or a drive (e.g., a disk drive, etc.). Electronic storage may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage may include one or more virtual storage resources (e.g., cloud storage, a virtual private network, and/or other virtual storage resources). Electronic storage may store machine-readable instructions, software algorithms, information determined by processor(s), information received from server(s), information received from computing platform(s), and/or other information that enables server(s) to function as described herein. The electronic storage can also be accessible via a network connection.

Processor(s) may be configured to provide information processing capabilities in server(s). As such, processor(s) may include one or more of a digital processor, an analog processor, a digital circuit designed to process information, an analog circuit designed to process information, a state machine, and/or other mechanisms for electronically processing information, such as FPGAs or ASICs. The processor(s) may be a single entity, or include a plurality of processing units. These processing units may be physically located within the same device, or processor(s) may represent processing functionality of a plurality of devices operating in coordination or software functionality.

The processor(s) can be configured to execute machine-readable instruction or learning modules by software, hardware, firmware, some combination of software, hardware, and/or firmware, and/or other mechanisms for configuring processing capabilities on processor(s). As used herein, the term "machine-readable instruction component" may refer to any component or set of components that perform the functionality attributed to the machine-readable instruction component. This can include one or more physical processors during execution of processor readable instructions, the processor readable instructions, circuitry, hardware, storage media, or any other components.

The server 306 can be configured with machine-readable instructions 312 having one or more functional modules. The machine-readable instructions 312 can be implemented on one or more servers 306, having one or more processors 310, with access to memory 308. The machine-readable instructions 312 can be a single networked node, or a machine cluster, which can include a distributed architecture of a plurality of networked nodes. The machine-readable instructions 312 can include control logic for implementing various functionality, as described in more detail below. The machine-readable instructions 312 can include a drug identification module 314, a wayfinding module 316, an image learning module 318, a task management module 320, a content module 322, a verification module 324, and a biometric module 326.

The task management module 320, can be configured to receive a prescription fulfillment request, assign the prescription fulfillment request to the user for fulfillment, and indicate the status of the prescription fulfillment. An electronic prescription (eScript) or hardcopy prescription can be received by a pharmacy. The prescription can contain prescription information, such as drug name or identifier, drug dosing, drug pill count, and patient name or identifier, among others. The pharmacy can then generate a fulfilment request including the prescription information that can be received by the task management module 320 of the server 306. The task management module 320 can assign a particular prescription fulfillment task to a user (pharmacist or staff). The task management module 320 can load balance fulfillment workloads across a plurality of users. The task management module 320 can indicate the status of the prescription fulfillment.

The drug identification module 314, can be configured to identify, via the server, a drug identified in the prescription fulfillment request and retrieve drug-related information from a standardized drug database related to the identified drug. The drug identification module 314 can be operably connected to a standardized drug database (not shown) that can be configured to store standardized drug information. The standardized drug database can be accessed via a local area network, wide area network, application programming interface, or other suitable communication mechanism. Standardized drug information can include drug product data, drug images, pricing information, professional monographs, patient education, and clinical decision support data, among other information.

The image learning module 318, can be configured to analyze a video camera image to determine a pill count, identify biometric features of an individual, or other suitable information. The image learning module 318 can receive, via the wearable device 100 over an encrypted network, an image of a plurality of pills (with a pill size, shape, color, marking, etc.) as the user wearing the wearable device 100 pours pills out to count them. Using the standardized drug information from the drug identification module 314, the pill count can be determined by correlating one or more pill characteristics from the standardized drug information with the image of a plurality of pills. The correlation can include matching the size, shape, or other relevant attributes.

The image learning module 318 can also receive, via the wearable device over an encrypted network, an image of a drug label having drug-identifying information for that drug. A drug label image can include an image of a drug barcode, a drug identifier, a drug name, a drug expiration date, a manufacture name, or other relevant information. Additionally, the image learning module 318 can receive, via the wearable device over an encrypted network, an image of a user, patient, or customer. For example, the video camera 108 on the wearable device 100 can capture an image of a user (e.g., face, retina, etc.) as the user puts on the wearable device 100. The image learning module 318 can determine and store facial landmarks for the user for use by the biometric module 326. Additionally, the video camera 108 on the wearable device 100 can capture an image of a customer (e.g., face, retina, etc.) as the customer approaches the user wearing the wearable device 100. The image learning module 318 can detect and store facial landmarks for a person (customer, patient, etc.) for use by the biometric module 326. Should one or more images be blurred or otherwise unintelligible, the image learning module 318 can receive a new image from the wearable device 100. The image learning module 318 can also detect identifying information from other biometric sources, such as video of a user walking, or other suitable information. Additionally, the image learning module 318 can receive video from the video camera 108 of the wearable device 100 showing hand gestures and translate the gestures into system actions by correlating the captured hand gesture with one or more stored hand gesture videos or mathematical representations of a gesture.

The content generation module 322, can be configured to send and receive images, audio, and text related to the prescription fulfillment request to and from the wearable device 100. The content generation module 322 can generate one or more virtual elements for display on the transparent display 106. The virtual elements are displayed on the transparent display 106 such that real-world objects can still be seen. Real-world objects can be over-laid with virtual reality elements to provide additional information to the user. For example, alerts can be generated by the content generation module 322 and displayed on the wearable device 100, indicating whether the drug-identifying information on the drug label matches the drug identified in the fulfillment request or whether the pill count matches the fulfillment request drug pill count. Additionally, system icons can be displayed on the transparent display 106 for interaction with the user using the input element 120, or hand gestures captured by the video camera 108 and processed by the image learning module 318. The content generation module 322 can also display prescription or standardized drug-related information, and wayfinding information on the transparent display 106.

The verification module 324, can be configured as a quality control mechanism to verify fulfillment, identification, wayfinding, or other suitable data. The verification control module can correlate actual measured data with the calculated expected data to verify that the appropriate outcome is achieved. The measured data can include accuracy of the fill, time spent on each task, and time spent between each task, among others. The expected data can include predetermined data stored in the memory, including the designated time for each task, and the designated time between each task, among others. The verification module 324 can also track analytics related to a user, including error rate, time to fill, and number of completed fulfilments, among other measurables.

The biometric module 326, can be configured to identify the user or a patient using data captured by the wearable device 100. The captured data can include, an image, audio, video, or other suitable data. The biometric module can work in concert with the image learning module 318. The image of the user received by the image learning module 318 can be correlated by the biometric module 326 against a user database stored in memory 308 for authentication purposes, such as allowing access to the pharmacy system. The image of the customer received by the image learning module 318 can be correlated by the biometric module 326 against a user database stored in memory 308 or other third-party biometric database to identify the customer.

The wayfinding module 316, can be configured to determine a route from the user's position to the identified drug's shelf location, the route displayed on the transparent display. The pharmacy floor plan can be entered in to the augmented reality pharmacy system 300 via a user interface provided by the wayfinding module 316. The shelving system can also be entered into the wayfinding module 316 via a user interface. A 3-D representation of the pharmacy facility can thereby be stored in the augmented reality pharmacy system 300 by the wayfinding module 316. Each position on the shelf can be identified by the wayfinding module 316 using a location name and an assigned drug, or other suitable information. So, when a user receives a fulfillment request, the content generation module 322 can determine a route between the user and the drug identified for fulfillment. The wearable device 100 can include a GPS device or an RFID device so that the wayfinding module 316 can determine the user's location. The wearable device 100 can also determine the user's location by triangulating signals received from the wearable device 100 using Wi-Fi or Cellular technology. The route can be generated by the content generation module 322 and displayed on the wearable device 100. The position of the identified drug on the shelf can be highlighted by the content generation module 322 and displayed on the wearable device 100 to minimize the search time of the user.

Figure 4:
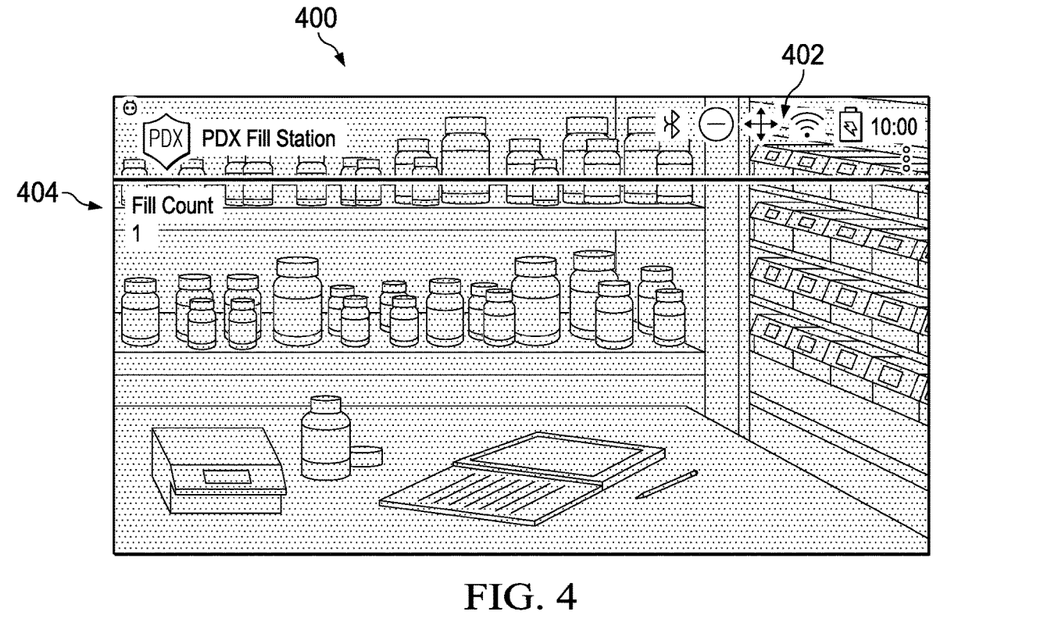
FIG. 4 illustrates a user's view through a wearable device, in accordance with one exemplary embodiment of the present disclosure.

FIG. 4 illustrates a user's view 400 through a wearable device 100, in accordance with one exemplary embodiment of the present disclosure. The content generation module 322 can generate one or more virtual elements for display on the transparent display 106, such that real-world objects can be seen along with generated virtual elements to provide additional information to the user. For example, the wearable device 100 can show the real-world space of the user (e.g. desks, pill bottles, and other office equipment) along with generated content, such as system indicators 402 and task fulfilment information 404. System indicators 402 can include battery life, time, network connectivity, alerts, among other suitable indicators. Task fulfillment indicators 404 can include the user name, user identifier, task number, fulfilment tasks assigned, and fulfillment tasks completed, among other suitable indicators. Additionally, an audible alert can be provided to the user via the earpiece 112, welcoming the user and audibly providing other relevant task information, such as the user name, user identifier, task number, fulfilment tasks assigned, and fulfillment tasks completed, among other suitable information.

Figure 5:
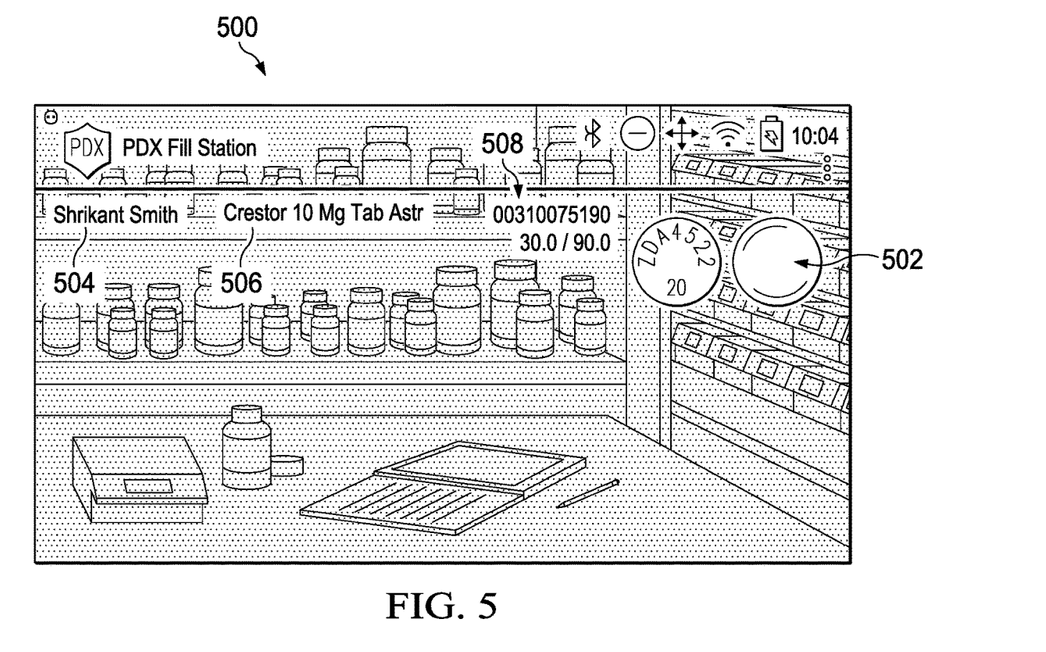
FIG. 5 illustrates a user's view through a wearable device, having drug information displayed, in accordance with one exemplary embodiment of the present disclosure.

FIG. 5 illustrates a user's view 500 through a wearable device, having drug information displayed, in accordance with one exemplary embodiment of the present disclosure. The content generation module 322 can generate one or more virtual elements for display on the transparent display 106, such that real-world objects can be seen along with generated virtual elements to provide additional information to the user. For example, the wearable device 100 can show the real-world space of the user (e.g. desks, pill bottles, and other office equipment) along with generated content, such as pill images 502, task fulfillment information 504, drug information 506, and prescription information 508. One or more pill images 502 can be retrieved from the standardized drug database and displayed on the wearable device to provide a drug reference for the user when filling the prescription. Task fulfillment indicators 504 can include the user name, user identifier, task number, fulfilment tasks assigned, and fulfillment tasks completed, among other suitable indicators. Drug information 506 can include the name, dosage, form, and other information relevant to the identified drug. Prescription information 508 can include the prescription number, pill count, refill count, and other relevant information. Additionally, an audible alert can be provided to the user via the earpiece 112, announcing the prescription information and audibly providing other relevant information, such as task identification, next steps, and other suitable information.

Figure 6:
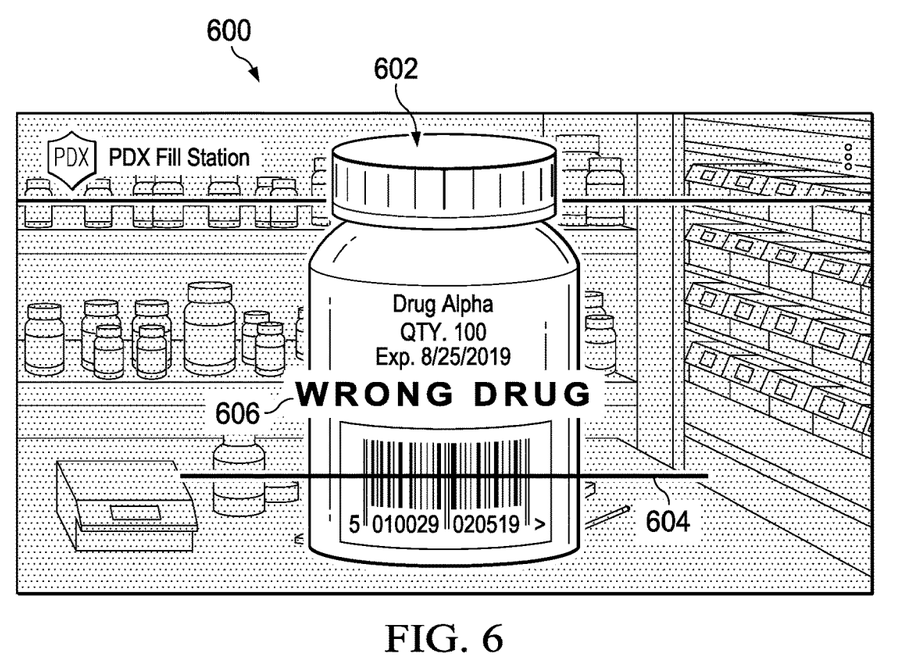
FIG. 6 illustrates a user's view through a wearable device, having a drug label within view, with an alert displayed, in accordance with one exemplary embodiment of the present disclosure.

FIG. 6 illustrates a user's view 600 through a wearable device, having a drug label within view, with an alert displayed, in accordance with one exemplary embodiment of the present disclosure. The content generation module 322 can generate one or more virtual elements for display on the transparent display 106, such that real-world objects can be seen along with generated virtual elements to provide additional information to the user. For example, the wearable device 100 can show the real-world space of the user (e.g. desks, pill bottles, and other office equipment) along with generated content, such as a task action artifact 604 and alerts 606. Once a user has acquired a drug bottle 602 for fulfillment of a prescription, the user can receive a task action artifact 604 indicating the next action, such as aligning the drug label of a pill bottle 602 with a task action artifact 604 to verify whether the correct drug bottle was retrieved. An alert can be displayed on the transparent display 106 related to the present task, such as whether the drug-identifying information on the drug label of the pill bottle 602 matches the drug identified in the fulfillment request. Additionally, an audible alert can be provided to the user via the earpiece 112, announcing the action to be performed, whether the drug-identifying information on the drug label of the pill bottle 602 matches the drug identified in the fulfillment request, or audibly providing other relevant information, such as task identification, next steps, and other suitable information.

Figure 7:
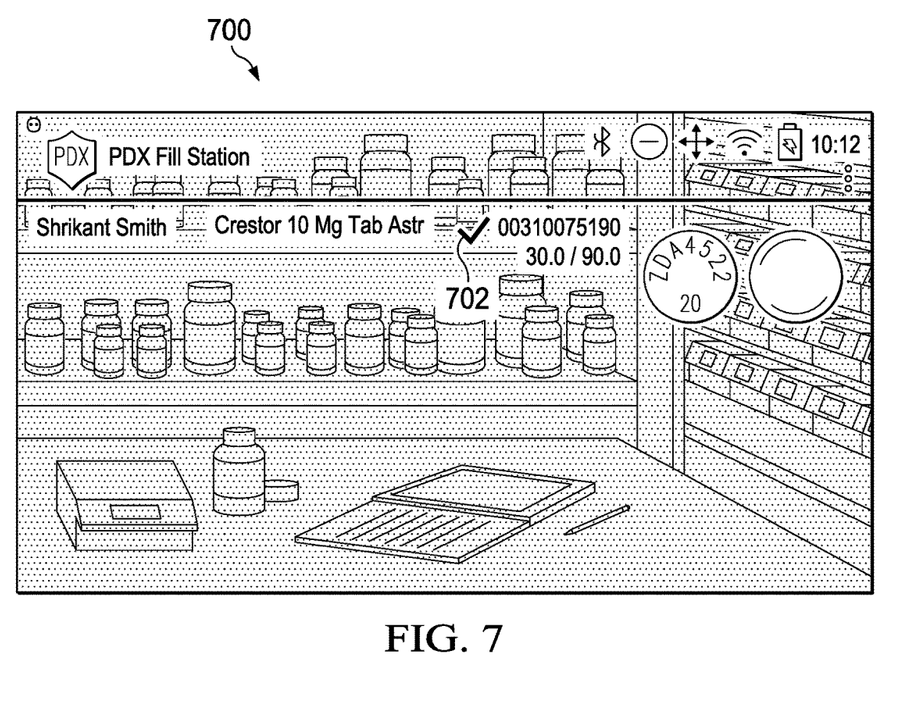
FIG. 7 illustrates a user's view through a wearable device, having verification information displayed, in accordance with one exemplary embodiment of the present disclosure.

FIG. 7 illustrates a user's view 700 through a wearable device, having verification information displayed, in accordance with one exemplary embodiment of the present disclosure. The content generation module 322 can generate one or more virtual elements for display on the transparent display 106, such that real-world objects can be seen along with generated virtual elements to provide additional information to the user. For example, the wearable device 100 can show the real-world space of the user (e.g. desks, pill bottles, and other office equipment) along with generated content, such as an alert indicating whether the pill count matches the fulfillment request drug pill count or a completion alert 702 indicating that the fulfillment task has been completed for the received prescription. Additionally, an audible alert can be provided to the user via the earpiece 112, announcing whether the pill count matches the fulfillment request drug pill count, whether the fulfillment task has been completed for the received prescription, or audibly providing other relevant information, such as task identification, next steps, and other suitable information.

Figure 8:
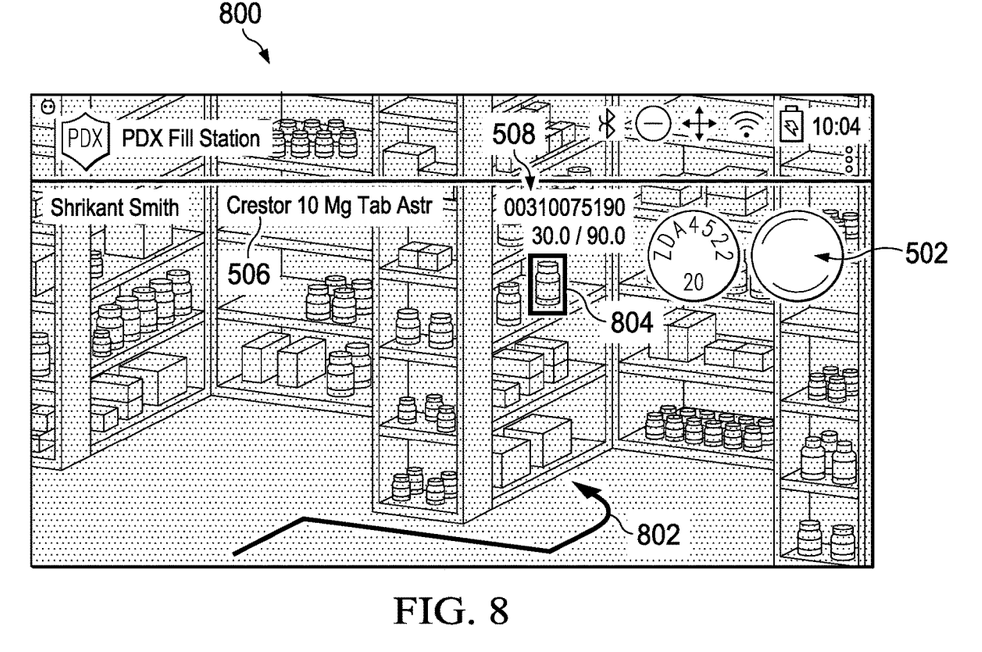
FIG. 8 illustrates a user's view through a wearable device, having wayfinding information displayed, in accordance with one exemplary embodiment of the present disclosure.

FIG. 8 illustrates a user's view 800 through a wearable device, having wayfinding information displayed, in accordance with one exemplary embodiment of the present disclosure. The content generation module 322 can generate one or more virtual elements for display on the transparent display 106, such that real-world objects can be seen along with generated virtual elements to provide additional information to the user. For example, the wearable device 100 can show the real-world space of the user (e.g. desks, pill bottles, and other office equipment) along with generated content, such as wayfinding information showing a route from the user's location to the location of a pill bottle for fulfillment of the received prescription. The wayfinding module 316, can be configured to determine a route 802 from the user's position to the identified drug's shelf location, the route 802 can be displayed on the transparent display. The route 802 can be generated by the content generation module 322 and displayed on the wearable device 100 using the pharmacy floor plan and predetermined wayfinding shapes that can connect one or more landmarks having RFID or other suitable technology disposed therein. Alternatively, landmarks can be coded into the content generation module 322. The position of the identified drug on the shelf can include a highlighted artifact 804 generated by the content generation module 322 and displayed on the wearable device 100 to minimize the search time of the user.

Figure 9:
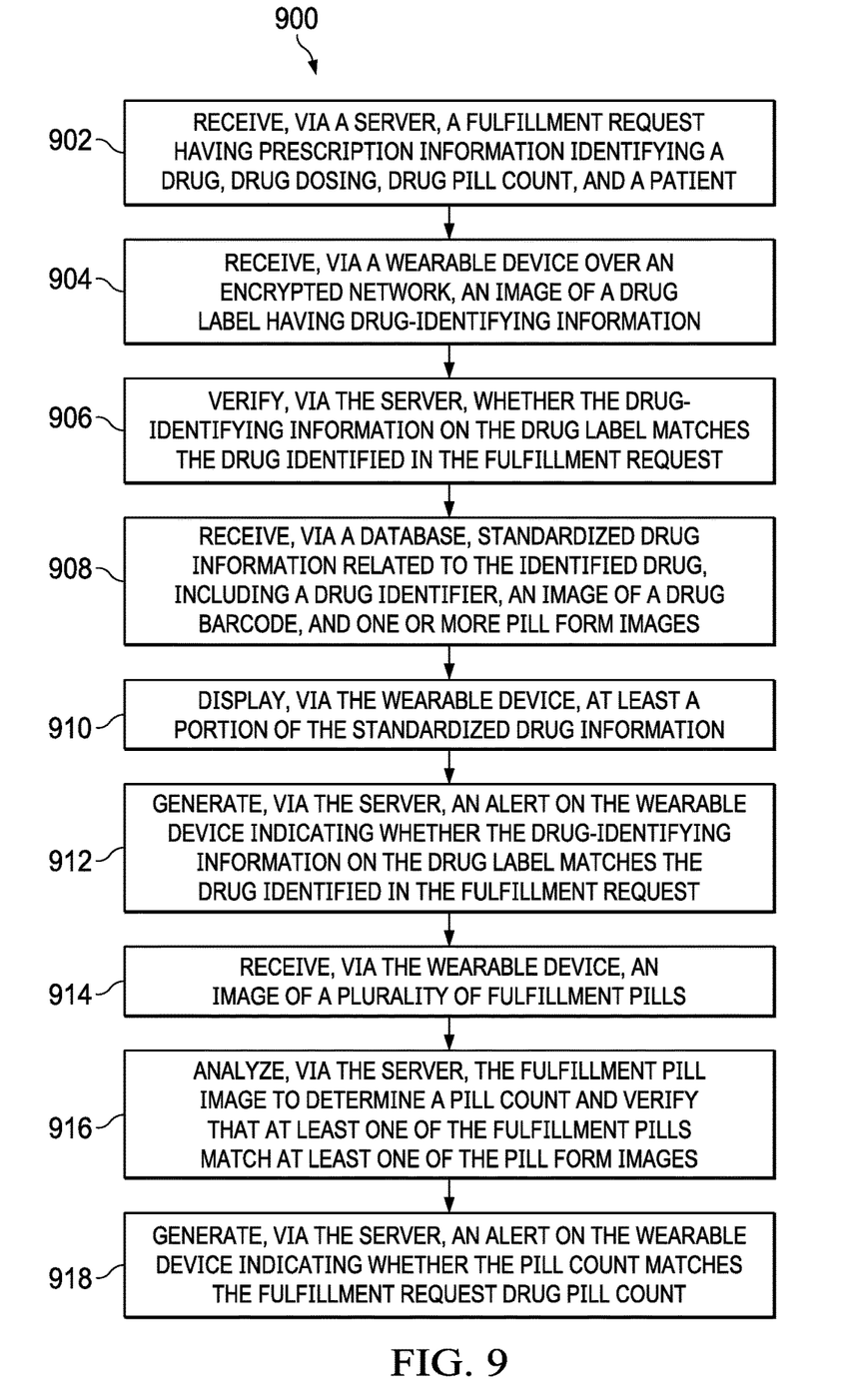
FIG. 9 illustrates a flow chart diagram for processing a fulfilment request, in accordance with one exemplary embodiment of the present disclosure.

FIG. 9 illustrates a flow chart diagram 900 exemplifying control logic embodying features of a method for processing a fulfilment request, in accordance with one exemplary embodiment of the present disclosure. The prescription fulfillment control logic 900 can be implemented as an algorithm on a server, a machine learning module, or other suitable system. The prescription fulfillment control logic 900 can be achieved with software, hardware, an application programming interface (API), a network connection, a network transfer protocol, HTML, DHTML, JavaScript, Dojo, Ruby, Rails, other suitable applications, or a suitable combination thereof.

The prescription fulfillment control logic 900 can leverage the ability of a computer platform to spawn multiple processes and threads by processing data simultaneously. The speed and efficiency of the prescription fulfillment control logic 900 is greatly improved by instantiating more than one process to generate a record having a patient's data. However, one skilled in the art of programming will appreciate that use of a single processing thread may also be utilized and is within the scope of the present invention.

The prescription fulfillment control logic 900 process flow of the present embodiment begins at step 902, where the control logic can receive, via a server, a fulfilment request having prescription information identifying a drug, drug dosing, drug pill count, and a patient. The fulfillment request can be received from an EMR, web portal, or other suitable mechanism. The prescription information can include a dosage amount, drug administration information, or other suitable information. The control logic then proceeds to step 904.

At step 904, the prescription fulfillment control logic 900 can receive, via a wearable device 100 over an encrypted network, an image of a drug label having drug-identifying information. The image can be captured via video camera 108. The prescription fulfillment control logic 900 can access the wearable device 100 via a network connection or other suitable means. The control logic then proceeds to step 906.

At step 906, the prescription fulfillment control logic 900 can verify, via the server, whether the drug-identifying information on the drug label matches the drug identified in the fulfillment request. The prescription fulfillment control logic 900 can correlate the information on the drug label with the prescription information by comparing one or more related fields of the two to identify whether they match. For example, the prescription fulfillment control logic 900 can calculate the differences, standard deviation, average, interpolation, or other data analysis, on the information to set or modify the thresholds. The control logic then proceeds to step 908.

At step 908, the prescription fulfillment control logic 900 can receive, via a database, standardized drug information related to the identified drug, including a drug identifier, an image of a drug barcode, and one or more pill form images. The standardized drug database can be accessed via a local area network, wide area network, application programming interface, or other suitable communication mechanism. Standardized drug information can include drug product data, drug images, pricing information, professional monographs, patient education, and clinical decision support data, among other information. The one or more fields of each of the databases for the identified drug may have variations, such that the fields do not match exactly. The control logic then proceeds to step 910.

At step 910, the prescription fulfillment control logic 900 can display, via the wearable device, at least a portion of the standardized drug information. One or more pill images 502 can be retrieved from the standardized drug database and displayed on the wearable device to provide a drug reference for the user when filling the prescription. Standardized drug information can include the name, dosage, form, and other information relevant to the identified drug. Prescription information 508 can include the prescription number, pill count, refill count, and other relevant information. The control logic then proceeds to step 912.

At step 912, the prescription fulfillment control logic 900 can generate, via the server, an alert on the wearable device 100 indicating whether the drug-identifying information on the drug label matches the drug identified in the fulfillment request. The alert can be visual or audible. The control logic then proceeds to step 914.

At step 914, the prescription fulfillment control logic 900 can receive, via the wearable device, an image of a plurality of fulfilment pills. The image learning module 318 can receive, via the wearable device 100 over an encrypted network, an image of a plurality of pills (with a pill size, shape, color, marking, etc.) as the user wearing the wearable device 100 pours pills out to count them. The control logic then proceeds to step 916.

At step 916, the prescription fulfillment control logic 900 can analyze, via the server, the fulfilment pill image to determine a pill count and verify that at least one of the fulfillment pills match at least one of the pill form images. Using the standardized drug information from the drug identification module 314 as training information for image processing, the number of pills before the user can be determined. The control logic then proceeds to step 918.

At step 918, the prescription fulfillment control logic 900 can generate, via the server, an alert on the wearable device indicating whether the pill count matches the fulfillment request drug pill count. The alert can be visual or audible. The control logic then terminates or awaits a new prescription request and can repeat the aforementioned steps.

The present disclosure achieves at least the following advantages:
1. Improves pharmacy fulfilment error rates by providing image processing systems adapted to characterize prescription and drug related information to verify prescription fulfillment;
2. Incorporates augmented reality systems with pharmacy systems to provide enhanced fulfillment systems where real-world objects can be over-laid with virtual reality elements to provide additional pharmaceutical information to a user; and
3. Shortens time spent looking for a specific drug bottle in a maze of similar-looking drug bottles by incorporating wayfinding technology coupled with location based components.

Persons skilled in the art will readily understand that these advantages and objectives of this system would not be possible without the particular combination of computer hardware and other structural components and mechanisms assembled in this inventive system and described herein. It will be further understood that a variety of programming tools, known to persons skilled in the art, are available for implementing the control of the features and operations described in the foregoing material. Moreover, the particular choice of programming tool(s) may be governed by the specific objectives and constraints placed on the implementation plan selected for realizing the concepts set forth herein and in the appended claims.

The disclosure may be embodied in other specific forms without departing from the spirit or essential characteristics thereof. For example, each of the new structures described herein, may be modified to suit particular local variations or requirements while retaining their basic configurations or structural relationships with each other or while performing the same or similar functions described herein. The present embodiments are therefore to be considered in all respects as illustrative and not restrictive. Accordingly, the scope of the inventions are established by the appended claims rather than by the foregoing description. All changes which come within the meaning and range of equivalency of the claims are therefore intended to be embraced therein. Further, the individual elements of the claims are not well-understood, routine, or conventional. Instead, the claims are directed to the unconventional inventive concept described in the specification.

What is claimed is:

1. An augmented reality pharmacy system, comprising:
a wearable device including a transparent display, a speaker, a video camera, a microphone, and an input element, the wearable device configured so that a user can see an object through the transparent display and information related to a pharmacy task on the transparent display; and
a server including computer-executable instructions configured to provide:
a task management module, configured to receive a prescription fulfillment request, assign the prescription fulfillment request to the user for fulfillment, and verify the prescription fulfillment,
a biometric module configured to identify the user or a patient using data captured by the wearable device,
a drug identification module, configured to identify, via the server, a drug identified in the prescription fulfillment request and retrieve drug-related information from a standardized drug database related to the identified drug including one or more pill form images,
a content generation module, configured to send and receive images, audio, and text related to the prescription fulfillment request including an image of a drug label having drug-identifying information and an image of a plurality of fulfillment pills to and from the wearable device,
an image learning module, configured to analyze a video camera image to determine a pill count,
a verification module configured to verify whether the drug-identifying information on the drug label matches the drug identified in the drug fulfillment request and to verify that at least one of the fulfillment pills match at least one of the pill form images; and
a wayfinding module, configured to determine and display a route from the user's position to the identified drug's shelf location, on the transparent display.

2. The augmented reality pharmacy system of claim 1, wherein the wearable device is in eyeglass form.

3. The augmented reality pharmacy system of claim 1, wherein the wearable device is in a handheld form.

4. The augmented reality pharmacy system of claim 1, wherein the speaker is disposed within an earpiece operably coupled to the wearable device.

5. The augmented reality pharmacy system of claim 1, further comprising an input element configured to allow the user to navigate menu elements displayed on the wearable device.

6. The augmented reality pharmacy system of claim 1, wherein the wearable device further comprises a wireless communication device or a wired communication device.

7. The augmented reality pharmacy system of claim 1, wherein the wearable device is configured to communicate with the server over an encrypted network.

8. The augmented reality pharmacy system of claim 1, wherein the wearable device further comprises a GPS device or an RFID device.

9. The augmented reality pharmacy system of claim 8, wherein the wayfinding module determines the user's location using the GPS device or the RFID device.

10. The augmented reality pharmacy system of claim 1, wherein the wearable device further comprises a gyroscope or accelerometer to identify the movement of the user.

11. The augmented reality pharmacy system of claim 1, wherein the image learning module determines facial landmarks for a user.

12. The augmented reality pharmacy system of claim 1, wherein the image learning module translates a hand gesture shown on video received from the wearable device into a system action by correlating the hand gesture with one or more stored hand gesture videos or mathematical representations of a gesture.

13. An augmented reality pharmacy fill station system, comprising:
    a wearable device configured to provide information related to a pharmacy task to a user; and
    a server including computer-executable instructions that when executed cause the server to:
        receive, via the server, a fulfillment request having prescription information identifying a drug, drug dosing, drug pill count, and a patient,
        receive, via the wearable device over an encrypted network, an image of a drug label having drug-identifying information,
        verify, via the server, whether the drug-identifying information on the drug label matches the drug identified in the fulfillment request,
        receive, via a database, standardized drug information related to the identified drug, including a drug identifier, an image of a drug barcode, and one or more pill form images,
        display, via the wearable device, at least a portion of the standardized drug information,
        generate, via the server, an alert on the wearable device indicating whether the drug-identifying information on the drug label matches the drug identified in the fulfillment request,
        receive, via the wearable device, an image of a plurality of fulfillment pills,
        analyze, via the server, the fulfillment pill image to determine a pill count and verify that at least one of the fulfillment pills match at least one of the pill form images, and
        generate, via the server, an alert on the wearable device indicating whether the pill count matches the fulfillment request drug pill count.

14. The augmented reality pharmacy fill station system of claim 13, wherein the server correlates the drug-identifying information with the prescription information by comparing one or more related fields of the drug-identifying information with one or more fields of the prescription information to identify whether they match.

15. The augmented reality pharmacy fill station system of claim 13, wherein the alert is visual.

16. The augmented reality pharmacy fill station system of claim 13, wherein the alert is audible.

17. The augmented reality pharmacy fill station system of claim 13, wherein the pill count is determined by correlating one or more pill characteristics from the standardized drug information with an image of a plurality of pills received from the wearable device.

18. A computer-implemented method for processing a fulfillment request, the computer-implemented method comprising:
    receiving, via a server, a fulfillment request having prescription information identifying a drug, drug dosing, drug pill count, and a patient;
    receiving, via a wearable device over an encrypted network, an image of a drug label having drug-identifying information;
    verifying, via the server, whether the drug-identifying information on the drug label matches the drug identified in the fulfillment request;
    receiving, via a database, standardized drug information related to the identified drug, including a drug identifier, an image of a drug barcode, and one or more pill form images;
    displaying, via the wearable device, at least a portion of the standardized drug information,
    generating, via the server, an alert on the wearable device indicating whether the drug-identifying information on the drug label matches the drug identified in the fulfillment request;
    receiving, via the wearable device, an image of a plurality of fulfillment pills,
    analyzing, via the server, the fulfillment pill image to determine a pill count and verify that at least one of the fulfillment pills match at least one of the pill form images; and
    generating, via the server, an alert on the wearable device indicating whether the pill count matches the fulfillment request drug pill count.

19. The method for processing a fulfillment request of claim 18, wherein the server verifies the drug-identifying information with the prescription information by comparing one or more related fields of the drug-identifying information with one or more fields of the fulfillment request.

20. The method for processing a fulfillment request of claim 18, wherein the alert is visual or audible.

* * * * *